United States Patent [19]

Imai et al.

[11] 4,275,252
[45] Jun. 23, 1981

[54] OXO ALCOHOL SYNTHESIS WITH RHODIUM CATALYST RECYCLE

[75] Inventors: Tamotsu Imai, Mt. Prospect; Edwin H. Homeier, Maywood; David E. Mackowiak, Des Plaines, all of Ill.

[73] Assignee: UOP Inc., Des Plaines, Ill.

[21] Appl. No.: 125,729

[22] Filed: Feb. 28, 1980

[51] Int. Cl.³ .......................................... C07C 27/22
[52] U.S. Cl. .................................................. 568/909
[58] Field of Search ....................................... 568/909

[56] References Cited

U.S. PATENT DOCUMENTS

| | | | |
|---|---|---|---|
| 3,369,050 | 2/1968 | Greene | 568/909 |
| 3,501,531 | 3/1970 | Wilkinson | 568/909 |
| 3,594,425 | 7/1971 | Brader et al. | 568/909 |
| 3,857,895 | 12/1974 | Booth | 568/909 |
| 3,896,047 | 7/1975 | Aycock et al. | 568/909 |
| 3,904,547 | 9/1975 | Aycock et al. | 568/909 |
| 3,954,877 | 5/1976 | Gipson | 568/909 |
| 4,061,687 | 12/1977 | Kaufhold et al. | 568/909 |

*Primary Examiner*—Joseph E. Evans
*Attorney, Agent, or Firm*—James R. Hoatson, Jr.; Raymond H. Nelson; William H. Page, II

[57] ABSTRACT

Alcohol may be synthesized from olefinic hydrocarbons by treating the hydrocarbon with carbon monoxide and hydrogen in a hydroformylation zone using a rhodium complex catalyst to effect the reaction. Following formation of the alcohol, the catalyst may be extracted from the alcohol by treatment with an aqueous ammonium hydroxide solution. The aqueous ammonium hydroxide solution containing the catalyst is then stripped of ammonia by treatment with a stripping agent such as carbon monoxide. A major portion of the alcohol is recovered while the remaining portion is used as an extractant to recover the rhodium complex catalyst from the aqueous ammonium hydroxide solution and thereafter is recycled to the hydroformylation zone.

15 Claims, 1 Drawing Figure

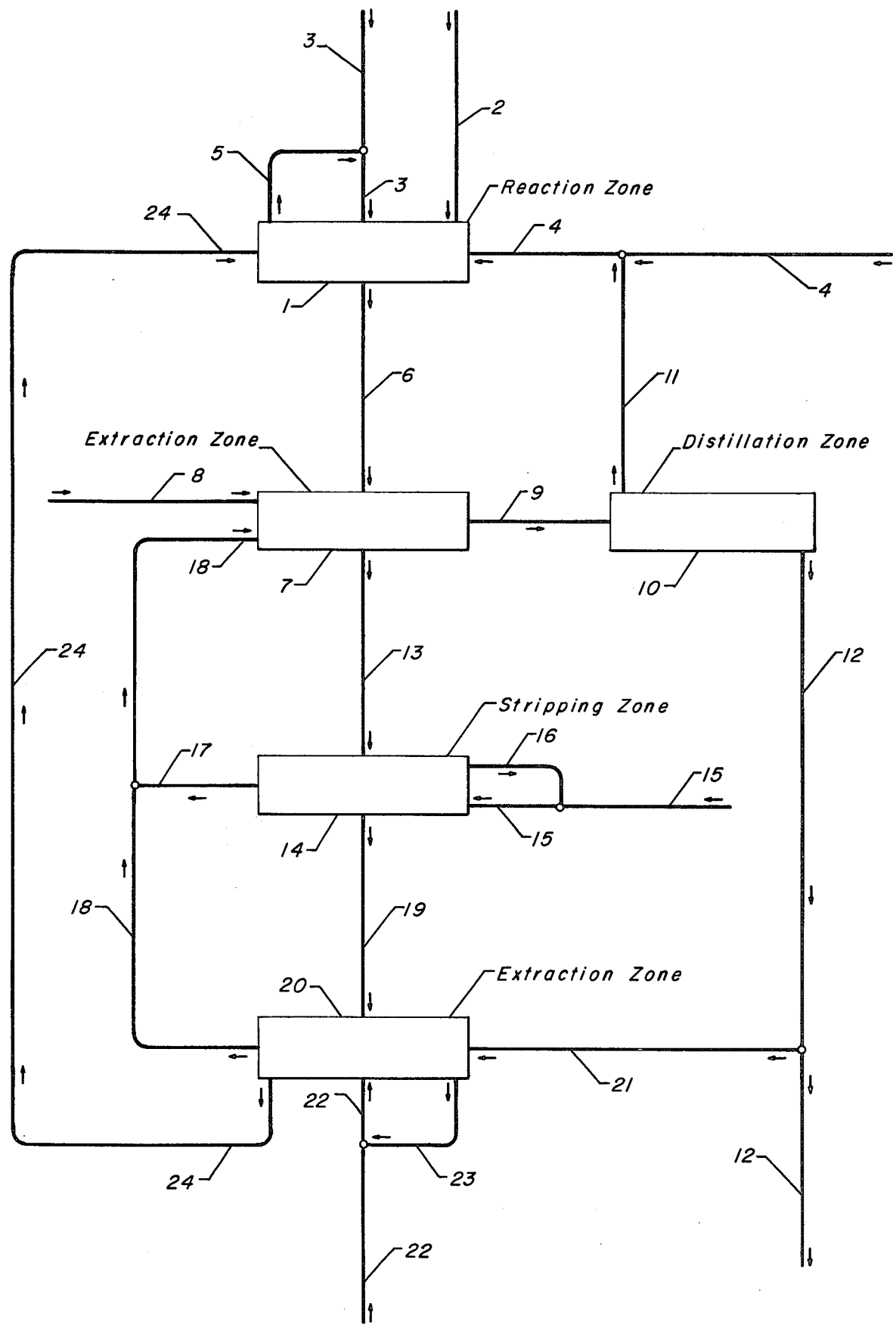

OXO ALCOHOL SYNTHESIS WITH RHODIUM CATALYST RECYCLE

This invention relates to a process for the synthesis of alcohols. More specifically the invention is concerned with a process for synthesizing alcohols by treating an olefinic hydrocarbon with carbon monoxide and hydrogen in the presence of a rhodium complex catalyst, said catalyst then being recovered in a series of steps hereinafter set forth in greater detail and recycled for further use.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, rocket fuel, beverages, etc. Isopropyl alcohol is used in the manufacture of acetone which in turn is a source of acetic anhydride, diacetone alcohol, methyl isobutyl ketone and other derivatives. It is also used as a solvent for essential oils, gums, resins; as a latent solvent for cellulose derivatives; as an antistalling agent in liquid fuels or as an intermediate in the manufacture of pharmaceuticals, perfumes, lacquers, rocket fuel, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, antifoam agent, as a perfume fixative for soaps and cosmetics as well as other uses.

The prior art has shown, as exemplified by the Oxo process, that aldehydes may be produced from olefinic hydrocarbons by treatment with carbon monoxide and hydrogen using a cobalt carbonyl catalyst. It has further been shown in the prior art, as exemplified by U.S. Pat. No. 2,880,241, that rhodium is known to be a much more active catalyst than cobalt. The activity and selectivity of rhodium catalysts may be altered by modifying the catalyst with other compounds such as tertiary amines. For example, when using tertiary amines to modify rhodium catalysts, it is possible to produce alcohols rather than aldehydes in this process.

The commercialization of processes for the synthesis of alcohols utilizing rhodium complex catalysts is affected by the difficulty which is attendant in the recovery of rhodium, a particular disadvantage which negates the commercial use of such catalyst complexes comprising the frequent losses of the precious metal which may occur under process conditions, the loss of only a trace amount of this precious metal making the process uneconomical to operate and overshadowing the technological attractive conversion rate and selectivity rate which is obtained when using this metal. The separation of the rhodium catalyst from alcohol products, especially high molecular weight alcohols by conventional means such as distillation, is not practical inasmuch as the unstable rhodium-amine complex decomposes in a distillation apparatus, thus resulting in the loss of the rhodium by plating or precipitation on the surfaces of the processing equipment.

Inasmuch as a particular advantage of utilizing a one-step synthesis of alcohol lies not only in a lower process cost and capital cost, when compared with the conventional Oxo process to produce aldehydes, but also results in a higher yield of the desired products. This is particularly advantageous inasmuch as a loss of aldehydes which easily takes place during distillation via their condensation in a still does not occur in this process.

It is therefore an object of this invention to provide a process for the synthesis of alcohol utilizing a recovery system for the catalyst.

A further object of this invention is found in a one step process for the synthesis of alcohols utilizing a precious metal catalyst such as a rhodium complex catalyst which is easily recoverable and reusable in the process.

In one aspect an embodiment of this invention resides in a process for the synthesis of an alcohol which comprises the steps of treating an olefinic hydrocarbon with carbon monoxide and hydrogen in a hydroformylation zone at hydroformylation reaction conditions in the presence of a rhodium complex catalyst; extracting said rhodium complex catalyst from the resulting alcohol by treatment with an aqueous ammonium hydroxide solution at treating conditions; stripping ammonia from said aqueous ammonium hydroxide solution containing said rhodium complex catalyst by treatment with a stripping agent at stripping conditions; recovering a major portion of said alcohol; and extracting said rhodium complex catalyst from said aqueous ammonium hydroxide solution at extraction conditions using the remaining portion of said alcohol as the extractant, and recycling said alcohol containing said rhodium complex catalyst to said hydroformylation zone.

A specific embodiment of this invention is found in a process for the synthesis of an alcohol which comprises treating hendecane with carbon monoxide and hydrogen in a hydroformylation zone at a temperature in the range of from about 50° to about 250° C. and a pressure in the range of from about 50 to about 300 atmospheres in the presence of a catalyst comprising chlorodicarbonylrhodium dimer, extracting said catalyst from the resulting dodecanol by treatment with an aqueous ammonium hydroxide solution at a temperature in the range of from about 20° to about 100° C. and a pressure in the range of from about atmospheric to about 50 atmospheres, stripping ammonia from said aqueous ammonium hydroxide solution which contains said catalyst by treatment with carbon monoxide at a temperature in the range of from about 20° to about 150° C. and a pressure in the range of from about 0.1 to about 5 atmospheres, recovering a major portion of said dodecanol, and extracting said catalyst from said aqueous ammonium hydroxide solution at a temperature in the range of from about 20° to about 200° C. and a pressure in the range of from about atmospheric to about 300 atmospheres using the remaining portion of said dodecanol containing said catalyst to the hydroformylation zone.

Other objects and embodiments will be found in the following further detailed description of the present invention.

As hereinbefore set forth the present invention is concerned with a process for the synthesis of alcohols utilizing a rhodium complex catalyst which may be recovered and recycled for further use. The synthesis of the alcohols is effected by reacting an olefinic hydrocarbon with carbon monoxide and hydrogen in the presence of these rhodium complex catalysts and a promoter or modifier comprising a tertiary amine. The reaction conditions which are employed to synthesize the alcohol will include a temperature of from about 50° to about 250° C. and a pressure in the range of from about 50 to about 300 atmospheres. In the preferred embodiment of the invention the pressures which are employed to effect the desired result will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 2000:1 moles of olefin per mole of catalyst and a mole ratio of tertiary amine modifier to catalyst in the range of from about 50:1 to about 300:1 moles of amine per mole of catalyst.

Examples of olefinic hydrocarbons which may be employed to effect the process of this invention will include straight chain olefins containing from 3 to about 30 carbon atoms such as propylene, butene-1, butene-2, pentene-1, pentene-2, hexene-1, hexene-2, hexene-3, heptene-1, heptene-2, heptene-3, octene-1, octene-2, octene-3, octene-4, nonene-1, nonene-2, nonene-3, nonene-4, as well as the isomeric decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc.

The reaction between the olefinic hydrocarbon of the type hereinbefore set forth, carbon monoxide and hydrogen is effected in the presence of a rhodium complex catalyst which may be organometallic in nature or which may comprise a salt which is converted to the complex catalyst during the process under the reaction conditions employed. Specific examples of these rhodium catalysts will include rhodium nitrate, rhodium chloride, rhodium bromide, rhodium iodide, rhodium fluoride, chlorodicarbonylrhodium dimer, rhodium carbonyl, chlorobis(ethylene)rhodium dimer, hexarhodiumhexadecylcarbonyl, tetrarhodiumdodecylcarbonyl, rhodium acetate, rhodium acetylacetonate, etc. The modifier which is utilized to selectively form alcohols will comprise a tertiary amine, said tertiary amine including alkyl amines, aryl amines, heterocyclic amines, cycloalkyl amines, etc., such as trimethylamine, triethylamine, tripropylamine, the isomeric tributylamines, tripentylamines, trihexylamines, triheptylamines, trioctylamines, trinonylamines, tridecylamines, dimethylethylamine, dimethylpropylamine, dimethylbutylamine, dimethyldodecylamine, triphenylamine, tribenzylamine, tri-o-tolylamine, tri-m-tolylamine, tri-p-tolylamine, tricyclopentylamine, tricyclohexylamine, N-methylpyridine, N-methylpyran, N-ethylpyridine, N-ethylpyran, etc. It is to be understood that the aforementioned olefinic hydrocarbons, rhodium catalysts and tertiary amines are only representative of the class of compounds which may be employed and that the present invention is not necessarily limited thereto.

After synthesizing the alcohol utilizing the desired reactants, catalysts and operating conditions, the product is recovered and the rhodium complex catalyst is separated therefrom and recovered by extracting the rhodium complex catalyst from the alcohol by treating the alcohol with an aqueous ammonium hydroxide solution. This step of the process is effected at treating conditions which will include a temperature in the range of from about ambient (20°-25° C.) to about 100° C. and a pressure in the range of from about atmospheric to about 50 atmospheres. In the event that superatmospheric pressures are employed in the treating step, the pressures are afforded by the introduction of a substantially inert gas such as nitrogen into the reaction vessel. After allowing the treatment to take place during a period which may range from about 0.5 up to about 20 hours or more, the aqueous ammonium hydroxide solution which contains from about 5 to about 50% by weight of ammonia is stripped of said ammonia by treatment with a stripping agent. The stripping of the ammonia from the aqueous ammonium hydroxide solution is accomplished inasmuch as if the ammonia is allowed to remain in the solution the interaction or chemical affinity between the ammonia and the rhodium present in the rhodium complex catalyst is so strong as to prevent the extraction of the rhodium catalyst with alcohol. The ammonia must be stripped from the solution so that less than about 0.5% by weight ammonia remains therein. By removing ammonia from the solution the rhodium complex will migrate from the aqueous ammonium hydroxide solution to the alcohol in a subsequent step hereinafter set forth in more detail. The stripping of the ammonia is accomplished by treatment with a stripping agent which may comprise carbon monoxide or a carbon monoxide-containing gas such as a mixture of carbon monoxide and hydrogen, carbon monoxide and nitrogen, carbon monoxide and helium, carbon monoxide and argon, etc. The stripping is effected at temperatures which may range from about ambient up to about 150° C. and at pressures ranging from about 0.1 to about 5 atmospheres.

Following the stripping of the ammonia the aqueous solution containing the rhodium complex catalyst and less than about 0.5% by weight of ammonia is then treated with a portion of the product alcohol which was formed during the hydroformylation reaction whereby the rhodium species is extracted from the aqueous ammonium hydroxide solution and recycled to the hydroformylation reaction zone. The extraction of the rhodium complex with the alcohol is also effected at extraction conditions which will include a temperature in the range of from about ambient to about 200° C. and a pressure in the range of from about atmospheric to about 300 atmospheres, the superatmospheric pressures being afforded by the use of a carbon monoxide containing gas, such as carbon monoxide or carbon monoxide mixed with other gases such as hydrogen, nitrogen, argon, helium, etc. As hereinbefore set forth the product alcohol containing the rhodium complex catalyst may then be used as a portion of the catalyst amount which is necessary to effect the hydroformylation reaction of an olefinic hydrocarbon with carbon monoxide and hydrogen in the hydroformylation reaction zone.

The process of this invention may be effected in any suitable manner and may comprise either a batch or continuous type operation. For example, when a batch type operation is used, a quantity of the olefin which is to be hydroformylated is charged to a pressure resistant apparatus such as an autoclave of the rotating, mixing or stirring type, said apparatus containing the rhodium complex catalyst and the tertiary amine which acts as a modifier. The autoclave is sealed and carbon monoxide and hydrogen pressured in until the desired operating pressure has been attained. Thereafter the reactor is heated to the desired operating temperature and maintained thereat for a predetermined period of time which may range from about 0.5 up to about 10 hours or more in duration. Following the completion of the desired reaction period, heating is discontinued and after the apparatus has returned to room temperature the excess pressure is discharged and the reaction mixture is recovered therefrom. The reaction mixture is then charged to a second apparatus which may also be of the pressure resistant type, if so desired, and the reaction mixture is contacted with an aqueous ammonium hydroxide solution at reaction conditions hereinbefore set forth in greater detail. Upon completion of the extraction or treatment period the aqueous ammonium hydroxide solution containing the extracted rhodium complex catalyst is separated from the organic phase which comprises the product alcohol and the amine modifier. The latter may then be subjected to fractional distillation to remove the amine modifier and passed to storage while the former is then placed in a third apparatus wherein the aqueous ammonium hydroxide solution containing the rhodium complex catalyst is stripped by treatment with carbon monoxide. The stripping operation is also effected at reaction conditions hereinbefore set forth for a period of time which may range from about 0.5 to about 10 hours or more in duration, the ammonia being removed during this time until an amount less than about 0.5% by weight remains. The substantially ammonia free aqueous hydroxide solution is then extracted with an alcohol which may comprise the product alcohol formed during the hydroformylation reaction or a dissimilar alcohol whereby the rhodium complex catalyst is extracted into the alcohol or organic phase which may then be used to form a portion of the catalyst in the hydroformylation reaction.

It is also contemplated within the scope of this invention that the process of the present invention may be effected in a continuous manner of operation. When such a type of operation is employed the starting material comprising olefinic hydrocarbon is continuously charged to a reaction zone which is maintained at the proper operating conditions of temperature and pressure and which contains a rhodium complex catalyst as well as a tertiary amine modifier. The desired operating pressures are attained by utilizing the autogenous pressures afforded by the carbon monoxide and hydrogen which are required for the hydroformylation reaction. After passage through the reaction zone for a predetermined period of time the reactor effluent is continuously withdrawn and passed to an extraction zone wherein said effluent is contacted or treated with an aqueous ammonium hydroxide solution also continuously charged to said zone. After passage through the extraction zone the aqueous layer comprising the ammonium hydroxide solution containing the rhodium complex catalyst is separated from the organic phase which comprises the product alcohol and the tertiary amine modifier. The latter is then continuously charged to a distillation zone wherein the tertiary amine modifier is separated from the product alcohol and recycled to the reaction zone while the product alcohol is withdrawn and a major portion thereof is recovered for storage. The aqueous phase is continuously charged to a stripping zone wherein it is contacted with carbon monoxide or a carbon monoxide-containing gas at stripping conditions whereby any free ammonia present in the ammonium hydroxide solution is stripped therefrom. The stripped aqueous ammonium hydroxide solution containing the rhodium complex catalyst is continuously withdrawn from the stripping zone and passed to a second extraction zone wherein it is contacted with a portion of the product alcohol which has been recovered from the distillation zone. In this extraction zone the rhodium complex catalyst is extracted and the alcohol or organic phase is then recycled to the hydroformylation zone wherein the rhodium complex catalyst affords a portion of the desired amount of catalyst required for the hydroformylation reaction. It is to be noted that the extraction of the rhodium complex catalyst from the aqueous ammonium hydroxide phase to the organic phase in the second extraction zone is also effected under a carbon monoxide pressure which may range from about atmospheric to about 300 atmospheres, thereby assuring a more complete extraction of the catalyst from the aqueous phase to the organic phase. The aqueous ammonium hydroxide solution may then be recycled back to the first extraction zone for use as the extractant in recovering the rhodium complex catalyst from the alcohol phase.

BRIEF DESCRIPTION OF THE DRAWING

The present invention will be further illustrated with reference to the accompanying drawing which sets forth a flow diagram of one embodiment of the process of this invention. It is to be understood that various valves, pumps, etc., have been eliminated as not being essential to the complete understanding of the invention. However, the utilization of these as well as other similar appurtenances will become obvious as the drawing is described.

Referring now to the drawing, an olefinic hydrocarbon which is to be hydroformylated according to the process of this invention is charged to reaction zone 1 through line 2 along with a rhodium complex catalyst of the type hereinbefore set forth. In addition, carbon monoxide and hydrogen are also charged to reaction zone 1 through line 3. In zone 1 the olefinic hydrocarbon is subjected to a hydroformylation reaction at conditions hereinbefore set forth in the presence of a rhodium complex catalyst which has been modified by the addition of a tertiary amine, said tertiary amine being charged to reaction zone 1 through line 4. After passage through the reaction zone for a predetermined period of time during which time any carbon monoxide and hydrogen which are used up in the reaction are recycled through line 5 back to line 3, the reaction mixture is withdrawn from zone 1 through line 6 and passed to a first extraction zone 7. In extraction zone 7 the organic phase is contacted with an aqueous ammonium hydroxide solution which is charged to reaction zone 7 through line 8. In extraction zone 7 any rhodium complex catalyst which has become entrained or dissolved in the organic phase is extracted therefrom. The organic phase which contains the product alcohol and the tertiary amine modifier are separated from the aqueous phase and withdrawn from zone 7 through line 9 and passed to distillation zone 10. In zone 10 the amine modifier is separated from the product alcohol and withdrawn through line 11 and recycled through lines 11 and 4 to reaction zone 1 for use therein to modify the catalyst. The product alcohol is withdrawn from distillation zone 10 through line 12 and a major portion thereof is passed to storage. The aqueous phase comprising an aqueous ammonium hydroxide solution containing the rhodium complex catalyst is withdrawn from extraction zone 7 through line 13 and passed to stripping zone 14. In stripping zone 14 the aqueous ammonium hydroxide solution is stripped of any free ammonia by contact with carbon monoxide or a carbon monoxide containing gas which is charged to zone 14 through line 15. The carbon monoxide or carbon monoxide-containing gas which is used to strip the ammonia from the aqueous ammonium hydroxide solution is separated therefrom and recycled through line 16 wherein it is admixed with makeup carbon monoxide entering through line 15. The ammonia which has been stripped from the aqueous ammonium hydroxide solution to the extent that the aqueous solution contains less than about 0.5% by weight of ammonia is withdrawn from stripping zone 14 through line 17 and recycled back to extraction zone 7 through lines 17 and 18.

The stripped aqueous ammonium hydroxide solution containing the rhodium complex catalyst is withdrawn from stripping zone 14 through line 19 and passed to a second extraction zone 20. In extraction zone 20 the aqueous ammonium hydroxide solution is contacted with a portion of the product alcohol which has been withdrawn from distillation zone 10 through line 12, said alcohol being charged to extraction zone 20 through line 21. The extraction of the rhodium complex catalyst from the aqueous phase to the organic phase in extraction zone 20 is also effected in the presence of carbon monoxide or a carbon monoxide-containing gas which is charged to extraction zone 20 through line 22. This carbon monoxide or carbon monoxide-containing gas may be charged to reaction zone 20 as a makeup, the major portion of the carbon monoxide being afforded by the recycle of carbon monoxide to extraction zone 20 through lines 22 and 23. The aqueous layer comprising the ammonium hydroxide solution is recycled from second extraction zone 20 through line 18 to first extraction zone 7. The organic phase which comprises the product alcohol containing the rhodium complex catalyst is withdrawn from extraction zone 20 and recycled through line 24 to reaction zone 1 wherein it is utilized as a portion of the catalyst in the hydroformylation of the olefinic hydrocarbon to form the desired alcohol.

The following examples are given to illustrate the process of the present invention. However, it is to be understood that these examples are given merely for purposes of illustration and that the present invention is not necessarily limited thereto.

EXAMPLE I

An olefin charge comprising 249.42 grams of a blend consisting of 94.4% by weight of normal hendecene, 3.4% by weight of normal hendecane, 1.6% by weight of aromatic impurities and 3.4% by weight of a normal eicosane internal standard were charged to a 3 liter rotating stainless steel autoclave along with 41.28 grams of dimethyldodecylamine and 0.26 grams of chlorodicarbonylrhodium dimer. The autoclave was sealed and 150 atmospheres of a 1:1 blend of carbon monoxide and hydrogen was charged thereto at room temperature. The autoclave was then heated to a temperature of 150° C. and maintained thereat for a period of 8 hours. At the end of this time, heating was discontinued and after the autoclave was allowed to return to room temperature the excess pressure was discharged and the reaction mixture was recovered therefrom. The deep red hydroformylation product was analyzed by standard gas liquid chromatographic techniques to determine that there had been a 100% conversion of olefin with a 91 mole % selectivity to dodecanol.

EXAMPLE II

In this example 74.92 grams of the alcohol product prepared according to Example I above along with 77.12 grams of an aqueous ammonium hydroxide solution containing 29% by weight ammonia were stirred in a glass flask. The dark green aqueous phase was separated from the organic phase in a separatory funnel under a nitrogen blanket. Analysis of the aqueous phase determined that it contained 309 parts/million of rhodium which was approximately 90% of the metal.

EXAMPLE III

The aqueous ammonium hydroxide solution containing the rhodium was then stripped by subjecting said solution to the action of carbon monoxide, said stripping of ammonia being effected at a temperature which ranged from 20° to 72° C., for about 100 minutes using a stream of 350 cc/min. of carbon monoxide. This was followed by vacuum distillation at a mercury pressure of 10 to 70 mm for a period of 75 minutes. The rhodium in the resultant aqueous solution, which contained less than 1% by weight of ammonia, was then placed in a rotating autoclave along with 5.17 grams of dodecanol. The autoclave was sealed and 100 atmospheres of carbon monoxide at room temperature was pressed into the autoclave which was then heated to a temperature of 100° C. The autoclave was maintained at this temperature for a period of 3 hours at the end of which time heating was discontinued. The excess pressure which had reached 119 atmospheres during the reaction period was released and the autoclave was opened. The recovered products were then separated into an aqueous phase and an alcohol phase in a separatory funnel under a blanket of nitrogen and analyzed for rhodium by atomic absorption analysis. This analysis determined that the rhodium distribution was 97.2 wt. % in the organic phase and 2.8% by weight in the aqueous phase. It was also noted that the organic product possessed the same dark red color as did the original alcohol product while the aqueous phase was clear and colorless.

EXAMPLE IV

To illustrate the ability of the recovered rhodium complex compound to act as a catalyst in a subsequent hydroformylation reaction, the above steps were repeated by subjecting hendecene to a hydroformylation reaction using chlorodicarbonylrhodium dimer as the catalyst and dimethyldodecylamine as a modifier in a manner similar to that hereinbefore set forth in Example I above. The resulting 1200 grams of product contained 692 parts/million by weight of rhodium, 81.6% by weight of dodecanol, 12.6% by weight of the modifier along with minor amounts of hendecane, aromatic impurities and an internal standard.

To extract the rhodium with aqueous ammonium hydroxide 105.2 grams of the product described in the above example along with 98.4 grams of a 29% aqueous ammonium hydroxide solution was stirred for a period of 16 hours at room temperature under a nitrogen blanket. At the end of this period stirring was discontinued and the aqueous and organic phases were allowed to separate under a nitrogen blanket. The organic phase which was recovered comprised 108.1 grams of a clear colorless alcohol and 93.7 grams of a dark green ammonium hydroxide solution containing 708 parts/million by weight of rhodium.

To strip the ammonia from the solution 86 grams of the dark green ammonium hydroxide solution was treated at a temperature ranging from 50° to 70° with a charge of 350 cc/min. of carbon monoxide for a period of 50 minutes followed by vacuum distillation at a temperature ranging from 70° to 60° C. under 188 mm of mercury pressure for 40 minutes. The resulting product comprising the dark green ammonium hydroxide solution contained only 0.046% by weight of ammonia.

Following this 23.55 grams of the substantially ammonia-free ammonium hydroxide solution containing the rhodium was extracted with 2.48 grams of 1-decanol in a stainless steel rotating autoclave at a temperature of 100° C. at a pressure of 129 atmospheres of carbon monoxide for a period of 0.5 hours. The product which was recovered from this treatment consisted of 22.98 grams of a colorless aqueous phase (rhodium-free ammonium hydroxide) and 2.30 grams of 1-decanol containing the extracted rhodium, said alcohol being bright red in color.

The 1-dodecanol (2.30 grams) along with 100.47 grams of hendecene and 16.9 grams of dimethyldodecylamine were placed in a rotating autoclave which was sealed and 150 atmospheres of a blend gas comprising a 1:1 mixture of carbon monoxide and hydrogen was purged thereto. The autoclave was heated to a temperature of 150° C. and maintained thereat for a period of 3 hours, the pressure during this time dropping from 156 atmospheres to 114. At the end of the 3 hour period heating was discontinued and after the autoclave had returned to room temperature the excess pressure was discharged and the autoclave was opened. The reaction product was subjected to standard gas liquid chromatography which determined that there had been a 100% conversion of the olefin with a 90.2 mole % selectivity to dodecanol.

We claim as our invention:

1. A process for the synthesis of an alcohol which comprises the steps of:
   (a) treating an olefinic hydrocarbon having at least 3 carbon atoms with carbon monoxide and hydrogen in a hydroformylation zone at hydroformylation reaction conditions in the presence of a rhodium complex catalyst and amine modifier to form an alcohol;
   (b) extracting said rhodium complex catalyst from the resulting alcohol by treatment with an aqueous ammonium hydroxide solution at treating conditions to obtain an organic phase comprising the product alcohol and amine modifier and an aqueous ammonium hydroxide solution phase containing said rhodium complex catalyst and thereafter separating the phases;
   (c) stripping ammonia from said aqueous ammonium hydroxide solution containing said rhodium complex catalyst by treatment with a stripping agent at stripping conditions;
   (d) recovering a major portion of said alcohol from the organic phase after removing the amine modifier therefrom; and
   (e) extracting said rhodium complex catalyst from said aqueous ammonium hydroxide solution at extraction conditions using the remaining portion of said alcohol as the extractant, and recycling said alcohol containing said rhodium complex catalyst to said hydroformylation zone.

2. The process as set forth in claim 1 in which said hydroformylation reaction conditions include a temperature in the range of from about 50° to about 250° C. and a pressure in the range of from about 50 to about 300 atmospheres.

3. The process as set forth in claim 1 in which said rhodium extraction conditions with an aqueous ammonium hydroxide solution include a temperature in the range of from about 20° to about 100° C. and a pressure in the range of from about atmospheric to about 50 atmospheres.

4. The process as set forth in claim 1 in which said stripping conditions include a temperature in the range of from about 20° to about 150° C. and a pressure in the range of from about 0.1 to about 5 atmospheres.

5. The process as set forth in claim 1 in which said rhodium extraction conditions with said portion of said alcohol include a temperature in the range of from about 20° to about 200° C. and a pressure in the range of from about atmospheric to about 300 atmospheres.

6. The process as set forth in claim 1 in which said olefinic hydrocarbon contains from 3 to about 30 carbon atoms.

7. The process as set forth in claim 1 in which said rhodium complex catalyst comprises chlorodicarbonylrhodium dimer.

8. The process as set forth in claim 1 in which said rhodium complex catalyst comprises rhodium carbonyl.

9. The process as set forth in claim 1 in which said aqueous ammonium hydroxide solution contains from about 5 to about 30% by weight of ammonia.

10. The process as set forth in claim 1 in which said stripping agent comprises carbon monoxide or a carbon monoxide-containing gas.

11. The process as set forth in claim 1 in which said olefinic hydrocarbon comprises hendecene and said alcohol comprises dodecanol.

12. The process as set forth in claim 1 in which said olefinic hydrocarbon comprises butene and said alcohol comprises pentanol.

13. The process as set forth in claim 1 in which said olefinic hydrocarbon comprises octene and said alcohol comprises nonanol.

14. The process as set forth in claim 1 in which said olefinic hydrocarbon comprises propene and said alcohol comprises butanol.

15. The process as set forth in claim 1 in which said olefinic hydrocarbon comprises nonadecene and said alcohol comprises eicosanol.

* * * * *